United States Patent [19]

Sadler et al.

[11] Patent Number: 4,880,007

[45] Date of Patent: Nov. 14, 1989

[54] CONTRAST AGENT FOR NMR SCANNING

[75] Inventors: Peter J. Sadler, Harrow Weald; Charles T. Harding, Bovington; James D. Kelly, Amersham; Andrew B. McEwen, Streatham, all of England

[73] Assignee: Amersham International PLC, Little Chalfont, United Kingdom

[21] Appl. No.: 884,622

[22] Filed: Jul. 11, 1986

[30] Foreign Application Priority Data

Jul. 19, 1985 [GB] United Kingdom ................. 8518300

[51] Int. Cl.$^4$ .............................................. A61K 49/00
[52] U.S. Cl. ........................................ 128/653; 424/9; 534/15
[58] Field of Search ................... 424/1.1, 2, 9; 534/15; 128/653, 654

[56] References Cited

U.S. PATENT DOCUMENTS

| 4,639,364 | 1/1987 | Hoey | 128/653 |
| 4,647,447 | 3/1987 | Gries et al. | 424/9 |
| 4,749,560 | 6/1988 | Elgavish | 128/653 |

FOREIGN PATENT DOCUMENTS

| 0071564 | 9/1983 | European Pat. Off. | 424/9 |
| 0133603 | 2/1985 | European Pat. Off. | 424/9 |
| 0169299 | 1/1986 | European Pat. Off. | 424/9 |
| 0173163 | 3/1986 | European Pat. Off. | 424/9 |

Primary Examiner—C. Fred Rosenbaum
Attorney, Agent, or Firm—Wenderoth, Lind & Ponack

[57] ABSTRACT

Complexes formed between (a) an amino di- or poly-phosphonate in which phosphonate groups comprise separate carbon atoms and (b) a paramagnetic metal ion such as $Gd^{3+}$, have calcified tissue seeking properties which make them useful as contrast agents for investigating bone metabolism by NMR scanning. Two preferred poly-phosphonates are ethylenediamine tetramethylphosphonate and meta-xylene-diamine tetramethylphosphonate.

21 Claims, No Drawings

CONTRAST AGENT FOR NMR SCANNING

This invention relates to a contrast agent for investigating calcified tissue by nuclear magnetic resonance (NMR) scanning. Contrast agents are used in NMR scanning to alter the $T_1$ and $T_2$ relaxation times of protons in their vicinity. Analysis of proton relaxation times is used to determine where in the body or other object being scanned the contrast agent has become located; and this in turn can provide information about the internal structure of the body. Calcified tissue contains relatively few protons as a result of low water content, and hence cannot be visualized in NMR scans. If a contrast agent could be caused to locate on or in calcified tissues and there to alter the $T_1$ or $T_2$ relaxation times of adjacent protons, it would be possible thereby to generate an NMR scanning image that might give valuable information about the state of the calcified tissues.

It is known that phosphates ($-O-PO_3H_2$) and phosphonates ($-C-PO_3H_2$) have an affinity for hydroxyapatite crystals, and thus tend to locate in vivo in regions of bone metabolism. In "Use of Radiolabelled Compounds in Medicine" Chapter 34, G. Subramanian et al., compare and contrast the properties as bone agents of complexes of di- and poly-phosphates and phosphonates with the radioactive isotope Tc-99m. Kits for preparing radioactive bone agents by labelling some of these di and poly-phosphates and phosphonates with Tc-99m are available commercially. In addition, mention can be made of European Patent Specification 122813 which describes ethylene glycol-1,2-bis phosphonic acid and its complex with Tc-99m as a bone seeking agent.

It is known that Tc-99m agents intended to locate in regions of bone metabolism can also locate in certain tumours, e.g. neuroblastoma, and other diseased tissues. Uptake of such agents in tumours is attributed to calcification in the tumours (Clinical Nuclear Medicine, 11, 337–40, 1986). As used herein, the term calcified tissue includes bone and regions of bone metabolism, and also regions of calcification in tumours and other diseased tissues.

Technetium is a transition metal in group 7B of the periodic table. It may reasonably be expected that other transition metal ions, including those with paramagnetic properties, will be capable of forming complexes with di- and poly-phosphonates.

EPA 133603 describes relaxation agents for modifying the contrasts obtained in medical imaging by NMR. These relaxation agents are complexes of paramagnetic metal ions with a variety of organic complexants including polyamino polymethylphosphonates. But no practical data are provided, nor is there any discussion of the biodistribution of the complexes.

In German Patent Specification DOS No. 3129906, there are described complexes of various geminal diphosphonates (that is to say, with two phosphonic acid groups attached to the same carbon atom) with ions of elements of atomic numbers 57 to 70, 21 to 29, 42 or 44. These complexes are stated to be suitable for administration to patients for NMR diagnosis, but no animal results are given. In particular, no indication is given of the toxicity of the complexes or of their solubility, which is important for administration. So far as biodistribution is concerned, it is merely stated that the complexes appear to be admirably suited for improved demarcation and location of lesions of the pancreas and liver and of tumours and haemorrhages in the cranial region. The possible use of poly-phosphonates for NMR bone scanning is not mentioned. In the light of the Schering disclosure, the following doubts remained:

(a) Di and poly-phosphonates are known to be toxic by reason of their ability to bind calcium ions. Similarly, most paramagnetic transition metal ions are toxic to a greater or lesser extent. Complexes of the two may be less toxic, but only provided that the complexes are stable in vivo. It was not predictable whether this would be the case.

(b) The complexes can only be useful for skeletal imaging by NMR if they tend to locate in regions of bone tissue. It was not known whether this would be the case.

(c) The complexes can only be useful for imaging by NMR if the complexed paramagnetic metal ion is nevertheless capable of altering the $T_1$ relaxation times of protons in its neighbourhood. It is known that complexing of the metal ions can reduce their activity in this respect. It was not possible to tell whether paramagnetic metal ions which were sufficiently strongly complexed to avoid toxicity problems would nevertheless retain the ability to alter proton relaxation times.

(d) The complexes can only be useful for skeletal imaging by NMR if they can be brought into solution in adequate concentrations at physiologically acceptable pH's. At least some of the complexes described are not sufficiently soluble.

According to the present invention, these doubts are resolved. The invention concerns a contrast agent for investigating calcified tissue by NMR scanning which agent comprises a complex formed between (a) an amino di- or poly-phosphonate in which phosphonate groups comprise different carbon atoms, and (b) a paramagnetic metal ion. The invention also concerns use of the complex for the preparation of the contrast agent. The invention also concerns the investigation of calcified tissue by NMR scanning following introduction of the contrast agent into the body. Some of the complexes are new compounds and are claimed as such.

Preferred di- or poly-phosphonates contain the groups $-N(CH_2PO_3H_2)_2$ at one or more, generally one or two, positions in the molecule. These phosphonates may have the formula:

$$YN(CH_2PO_3H_2)_2$$

or $$Z[N(CH_2PO_3H_2)_2]_2$$

where each of Y and Z may be an aliphatic or aromatic groups containing 1 to 12 carbon atoms which may also contain one or more hydroxyl, ether, carboxylate, sulphonate, amine or aminomethylphosphonate groups, or non-toxic salts thereof. Complexes containing aromatic groups are believed new.

A poly-phosphonate may for example have the general formula:

$$NX_2.CH_2.PO_3H_2$$

where the two groups X are the same or different and each is $-CH_2PO_3H_2$ or $-(CH_2)_nN(CH_2PO_3H_2)_2$, and n is up to 10, preferably 2 or 6, or a non-toxic salt thereof.

Examples of specific poly-phosphonates are nitrilotrimethylphosphonate, hexamethylene diamine tetramethylphosphonate (HDTMP), ethylene diamine tetramethylphosphonate (EDTMP), diethylene triamine pentamethylphosphonate (DTPMP), meta-xylene-diamine tetramethylphosphonate (MXDTMP), and non-toxic salts thereof.

Suitable paramagnetic metal ions are well known in the field and include those of the lanthanide elements with atomic numbers 58 to 70, and those of the transition metals with atomic numbers 21 to 29, 42 and 44. Preferred are Mn(II), Cu(II), Fe(II), Gd(III), Fe(III), Cr(III), Dy(III) and V(IV). Factors affecting the choice of metal ion are its paramagnetic properties, the stability and solubility of the metal ion phosphonate complex, its toxicity, and the extent to which the metal ion in the complex interacts with water so as to vary the proton relaxation times. The agents may also be used in a NMR chemical shift imaging technique.

The complexes are easily prepared, by mixing an aqueous solution of the chosen di- or poly-phosphonate with an aqueous solution of a salt of the chosen transition metal. Or a di- or poly-phosphonate may be added to an aqueous suspension of the transition metal carbonate. The precise structures of the complexes are not known with certainty, and may vary depending on the nature of reagents. The solutions may be buffered, generally at a pH in the range 4 to 10, and the mixture may be brought to a suitable pH for administration. Complex-formation takes place rapidly, and without the need for heating the mixed solutions.

Although equimolar amounts of the reagents may be used and give satisfactory results, in some cases it may be advantageous to use a higher molar concentration of the phosphate than of the metal ion. For example, in the case of the complex formed for EDTMP and Gd, it is preferred to use a molar ratio of EDTMP to Gd of at least 1.5. An upper limit for this ratio is set by the extent to which EDTMP is toxic and the amount of the complex to be administered. The toxic effects of excess EDTMP, or other phosphonates, are preferably countered by the incorporation of quantities of calcium within the formulation.

In order to investigate calcified tissue by NMR scanning, it may be necessary to administer, preferably by injection, an aqueous solution of the complex of from 0.5 to 250 mM, preferably 1 to 50 mM, concentration with respect to the paramagnetic metal ion. The volume for injection into a human subject is typically from 1 to 100 ml. If the desired quantity would be hypertonic if presented in a small volume for injection, then it may be converted to organic salt form, for example to the N-methyl glucamine salt, in accordance with known procedures.

The Examples below are organized as follows.

Example 1 described the preparation of three complexes according to the invention and shows that these are capable of altering proton relaxation times ($T_1$ and $T_2$).

Example 2 describes the preparation of other complexes, and uses radioactive $^{153}$Gd to demonstrate the extent to which these are bone-seeking in rats.

Example 3 describes the preparation of 12 further di- and poly-phosphonates.

Example 4 describes the preparation and proton T1 relaxation properties of complexes from the phosphonates of Example 3.

Example 5 describes the preparation and proton $T_1$ relaxation properties of hydroxy apatite adducts of complexes of Example 4.

The results indicate that the complexes are bone-seeking in vivo, and act in bound form as effective contrast agents for investigating calcified tissue by NMR scanning.

EXAMPLE 1 0.043 g Gd(NO$_3$)$_3$.5H$_2$O was mixed with 0.046 g EDTMP in 5 ml acetate buffer (pH 5.6). 1 ml 1M NaOH was added. To the clear solution a further 4 ml of acetate buffer was added to make the total volume 10 ml, (pH 5.6) containing 10 mM concentration of a complex designated Gd.EDTMP.

Similarly by using HDTMP and DTPMP there were prepared aqueous solutions of complexes designated Gd.HDTMP and Gd.DTPMP respectively. Binding studies, via observation of $T_1$ and $T_2$ relaxation times in water have shown that the metal:ligand complexes are in a 1:1 ratio.

In relaxation studies of the three complexes, the $T_1$ results obtained are set out in Table 1.

TABLE 1

| Concentration (mM) | $T_1$ (ms) at 200 MHz and 300° K. | | |
|---|---|---|---|
| | Gd.DTPMP | Gd.EDTMP | Gd.HDTMP |
| 5 | 23 | 18 | 30 |
| 2.5 | 38 | 38 | 71 |
| 1 | 45 | 87 | 142 |
| 0.5 | 144 | 168 | 284 |

The complexed Gd is clearly capable in all cases of altering $T_1$ relaxation times of proton in its neighbourhood.

Further studies were performed with Gd.EDTMP in a body scanner operating at 6 MHz. The $T_1$ relaxation time for water was determined as 1513 ms, whereas the $T_1$ relaxation time for a 0.1 mM Gd.EDTMP solution was determined as 722 ms. This confirms that the complexed Gd is capable of altering $T_1$ relaxation times of protons under conditions likely to be used in practice.

EXAMPLE 2

This example uses $^{153}$Gd to compare the biodistribution properties of various complexes in rats.

Equal volumes of 1 mM methylene diphosphonic acid and 0.5 mM Gd$^{3+}$ were used to prepare a complex designated Gd.MDP. The complex had poor solubility properties around physiological pH's.

Equal volumes of 10 mM ethane-1-hydroxy-1,1-diphosphonic acid and 5 mM Gd$^{3+}$ were used to prepare a complex designated Gd.EHDP. But the pH of the mixture had to be kept above 7 to avoid precipitation.

Equal volumes of 10 mM EDTMP and 5 mM Gd$^{3+}$ were used to prepare the complex Gd.EDTMP.

Using $^{153}$Gd, a comparison was made of certain properties of aqueous "solutions" of $^{153}$GdCl$_3$
$^{153}$Gd.MDP (0.5 mM with respect to Gd)
$^{153}$Gd.EHDP (5 mM with respect to Gd)
$^{153}$Gd.EDTMP (5 mM with respect to Gd)

The results are set out in Table 2. The biodistribution data there reported were obtained by means of an IV study in male rats which were sacrified two hours post injection. % activity per organ is given, together with ratios of bone to organ.

TABLE 2

| % Activity | $^{153}$Gd.Cl$_3$ | $^{153}$Gd.MDP | $^{153}$Gd.EHDP | $^{153}$Gd.EDTMP |
| --- | --- | --- | --- | --- |
| Bone | 38.6 | 3.1 | 22.64 | 45.2 |
| Muscle | 4.0 | 0.3 | 13.8 | 1.1 |
| Blood | 3.7 | 0.1 | 21.45 | 0.6 |
| Kidneys | 2.5 | 0.3 | 1.05 | 0.4 |
| Bladder & Urine | 12.5 | 1.0 | 24.0 | 45.8 |
| Lung | 0.6 | 0.4 | 1.55 | 0.1 |
| Liver & Spleen | 32.5 | 93.9 | 11.29 | 1.4 |
| Stomach & Gut | 3.9 | 0.0 | 4.21 | 1.9 |
| Carcass | 1.8 | 0.7 | 0.01 | 3.5 |
| Injection Site | 3.4 | 0.5 | 2.91 | 2.1 |
| RATIOS | | | | |
| Bone/Muscle | 83 | 80 | 14.07 | 491.2 |
| Bone/Blood | 12.2 | 33.2 | 1.24 | 173.0 |
| Bone/Liver & Spleen | 1.1 | 0.0 | 2.04 | 35.2 |

These results show that the complexes Gd.MDP and Gd.EHDP are not useful as bone scanning agents. On the other hand, the invention complex Gd.EDTMP is shown to be a good bone-seeking agent, and a good $T_1$ relaxation agent for water.

It is known that $Ca^{2+}$ can bind to di- and poly-phosphonates, and that this is one reason why these materials are toxic. It is also known that dimethylglucamine can be used to solubilize complexes of this kind. Checks on whether the bone uptake of the two complexes Gd.EDTMP and Gd.EHDP was affected by the addition (separately) to their aqueous solutions of $Ca^{2+}$ and dimethylglucamine; showed that neither addition had a significant effect.

EXAMPLE 3

The phosphonates listed below were synthesised by a direct Mannich type reaction using an amine, formaldehyde and phosphorous acid. The basic reaction is given in the paper by Moedritzer (JCS 1966 vol. 31 p 1603). The reaction is seen by $^{31}$PNMR to proceed quantitatively and isolation of the product was generally achieved by filtration and washing of the precipitate which forms during the reaction. In some cases isolation was achieved by concentration of the reaction mixture and in others by addition of ethanol to the concentrated reaction mixture. The method used is indicated below. The general reaction scheme is to heat the solution of the amine, phosphorous acid and concentrated HCl to reflux temperature. 100% excess of aqueous formaldehyde solution was then added over 1 hour. The reaction mixture is then refluxed for a further 1 hour and the product isolated.

Example para-xylene diamine tetramethylene phosphonate 41 g H$_3$PO$_4$ were dissolved in 100 ml of H$_2$O/concentrated HCl (50:50 v.v) and 17 g p-xylene diamine were added. The solution was brought to reflux and 80 ml formaldehyde solution 37% w/v were added over 1 hour. The solution was refluxed for a further hour during which precipitation of the product occurred. The solution was allowed to cool and the product filtered and washed with water, ethanol and ether, and dried at 100° C.

Yield 45.8 g
m.p. 249°-251° C.
Calculated for C$_{12}$H$_{26}$N$_2$O$_{12}$P$_4$, C 28.12, H4.69, N5.47, P24.21, Found C28.09, H4,79, N5.49, P24.04.

Ligands Synthesised

Amino ethanol dimethylene phosphonate-AEDMP
Glycine dimethylene phosphonate-GDMP
Gamma amino butyric acid dimethylene phosphonate-GABADMP
6-amino hexanoic acid dimethylene phosphonate-AHADMP
Meta-xylene diamine tetramethylene phosphonate-MXDTMP
Para-xylene diamine tetramethylene phosphonate-PXDTMP
1,3-diamino-2-hydroxy-propane tetramethylene phosphonate-DHPTMP
3,3'-diaminopropyl-N-methyl dipropylamine tetramethylene phosphonate-DPNDPTMD
4,9-Dioxa-1,12-dodecane-di-amine tetramethylene phosphonate DDDATMP
Di-propylene triamine pentamethylene phosphonate-DPTPMP
Triethylene tetramine hexamethylene phosphonate-TTHMP N,N'-bis(3 amine propyl) ethylene diamine hexamethylene phosphonate-BAPEDHMP

| Ligand | m.p. | Yield | Isolation | Form |
| --- | --- | --- | --- | --- |
| AEDMP | 235–237° C. | 40.1% | C | White crystals |
| GDMP | 200–201° C. | 60.8% | B | White crystals |
| GABADMP | 202–204° C. | 63.3% | B | White crystals |
| AHADMP | 192–194° C. | 84.4% | A | White crystals |
| MXDTMP | 238–239° C. | 74.2% | A | White crystals |
| PXDTMP | 249–250° C. | 76.5% | A | White crystals |
| DHPTMP | 272–275° C. | 60.5% | C | White crystals |
| DPNDPT | 228–230° C. | 65.1% | C | White crystals |
| DDDATMP | 145–147° C. | 70.3% | C | White crystals |
| DPTPMP | 195–299° C. | 58.8% | C | White crystals |
| TTMMP | 206–208° C. | 42.8% | B | Off white crystals |
| BAPEDHMP | 192–200° C. | 85.0% | C | White crystals |

Isolation
A-Crystallised out of reaction mixture
B-Crystallised out after reducing volume
C-Crystallised out after reducing volume and adding ethanol All products isolated as white/off white powders regular shapes under microscope.

EXAMPLE 4

1. The preparation of copper, nickel, manganese and cobalt complexes was achieved by heating the ligands, in suspension, with the metal carbonate.

Example

Preparation of manganese metaxylene diamine tetramethylene phosphonate.

2.6 g MXDTMP and 0.56 g of $MnCO_3$ were heated together in 200 ml $H_2O$ for 1 hour. The solvent was then removed under reduced pressure to produce a free flowing white powder.

Yield 2.65 g, Calculated for $C_{12}H_{28}N_2O_{12}P_4$, C23.08, H4.29, N4.62, P20.49, 96% recovery; Found C23.08, H4.13, N4.72, P19.51.

2. Complexes with metals such as chromium and gadolinium were systhesised by mixing equal molar quantities of ligand and metal salt. The methods differ in exact technique.

$Gd(NO_3)_3.5H_2O$ is added slowly to a solution of the sodium salt of the ligand at pH 7.0. There is precipitation but this is redissolved upon adding NaOH(dilute). Any suitable strength Gd phosphonate solution can be made in this way. Ligands containing less than four amino phosphonates were added at a concentration twice that of the metal with higher numbers of $-CH_2PO_3H_2$ groups the metal ligand ratio is 1:1. Chromium (Cr) complexes were made by boiling equimolar amounts of ligand and $Cr(NO_3)_3.9H_2O$ or in some cases ligand present in 2:1 excess as above. The reaction was seen to occur by noting the colour change blue to green. The mixtures were refluxed for 1-2 hours. The pale green precipitate was redissolved by addition of dilute NaOH to give a pH of about 7.0.

Relaxation Data 1

Relaxation measurements have been made on the phosphonate complexes at 200 MHz and 10 MHz a clinically relevant field strength.

| Chromium 200 MHz 25° C. 1 millimolar concentration | |
|---|---|
| Complexes | $T_1$ |
| Water Standard | 3.3s |
| $Cr(AEDMP)_2$ | 1.13s |
| $Cr(GDMP)_2$ | 0.89s |
| $Cr(GABADMP)_2$ | 0.91s |
| $Cr(AHADMP)_2$ | 1.04s |
| CrMXDTMP | 0.55s |
| Gadolinium Complex 200 MHz 25° C. 1 millimolar concentration | |
| GdMXDTMP | 0.064s |

Relaxation Data 2

| Manganese Complexes 200 MHz 25° C. 1 millimolar concentration | |
|---|---|
| | $T_1$ |
| Water Standard | 3.3s |
| $Mn(AEDMP)_2$ | 0.007s |
| $Mn(GDMP)_2$ | 0.160s |
| $Mn(GABADMP)_2$ | 0.072s |
| $Mn(AHADMP)_2$ | 0.125s |
| MnMXDTMP | 0.097s |

The aromatic ligand MXDTMP when complexed to metal results in efficient $T_1$ relaxations. The lines obtained at 200 MHz are sharp which implies less effect on $T_2$ relaxation. This would result in efficient $T_1$ relaxation but without loss of signal intensity due to line broadening.

Relaxation Data 3

Relaxation measurements have been made at 10 MHz at 37° C. for the complexes of MXDTMP at 10 mM concentration.

| | $T_1$ | $T_2$ |
|---|---|---|
| CrMXDTMP | 160 ms | 130 ms |
| MnMXDTMP | 10 ms | 9 ms |
| GdMXDTMP | 10 ms | 7 ms |

At 10 MHz 37° C. MXDTMP gives better relaxation than EDTMP.

| | $T_1$ | $T_2$ | $T_1/T_2$ |
|---|---|---|---|
| MnMXDTMP | 10 ms | 9 ms | 1.1 |
| MnEDTMP | 27 ms | 24 ms | 1.1 |
| 10 millimolar solutions | | | |

EXAMPLE 5

Binding to Hydroxy Apatite.

1 ml of hydroxy apatite solution 250 mg/ml in water was used for all the binding assays to described.

1. Binding of Ligands

The solid from 1 ml of hydroxy apatite solution was isolated by centrifugation and the supernatant removed. 0.41 ml of a 0.1M solution of ligand at pH 7.5±0.1 were than added and the solid resuspended. The solid was once more spun down and the supernatant analysed by $^{31}P$ NMR. This enabled the amount of bound phosphonate to be analysed.

2. Binding of Complexes

The procedure above was followed but this time 0.4 ml of 50 mM metal complex solution was added and the solid resuspended. The supernatant was analysed by $T_1$ using $T_1$ relaxation measurements and the amount bound to hydroxy apatite calculated.

3. Relaxation of Hydroxy Apatite-Complex Adducts

The binding studies above produced hydroxy apatite with phosphonate complexes bound. These solids were resuspended at 10 mg/ml and the $T_1$ and $T_2$ relaxation times measured at 10 MHz and 37° C.

Binding of Ligands to Hydroxy Apatite $^{31}P$ Study

| Ligand | % Bound to HAP |
|---|---|
| AEDMP | 50.9 |
| GDMP | 88.2 |
| GABADMP | 77.8 |
| AHADMP | 89.7 |
| EDTMP | 89.4 |
| BDTMP | 75.7 |
| MDTMP | 85.5 |
| ODTMP | 84.9 |
| MXDTMP | 84.1 |
| PXDTMP | 88.0 |

Binding of Chromium Complexes to Hydroxy Apatite

| Complex | | % Bound |
|---|---|---|
| None | (No $T_1$ change) | None |
| $Cr(AEDMP)_2$ | | 96% |
| $Cr(GDMP)_2$ | | 80% |
| $Cr(GABADMP)_2$ | | 90% |
| $Cr(AHADMP)_2$ | | 96% |

Relaxation of Hydroxy Apatite-Complex Adducts

| Complex | % Bound |
|---|---|
| CrMXDTMP | 96% |

| Complex 10 mg/ml | $T_1$ 10 MHz 37° C. | $T_2$ 10 MHz 37° C. |
|---|---|---|
| None HAP only | 2.50s | 0.97s |
| Cr(AEDMP)$_2$ | 1.03s | 0.53s |
| Cr(GDMP)$_2$ | 0.97s | 0.54s |
| Cr(GABADMP)$_2$ | 1.39s | 0.67s |
| Cr(AHADMP)$_2$ | 1.17s | 0.55s |
| CrMXDTMP | 0.98s | 0.56s |
| Mn(AEDMP)$_2$ | 0.14s | 0.12s |
| Mn(GDMP)$_2$ | 0.24s | 0.24s |
| Mn(GABADMP)$_2$ | 0.24s | 0.16s |
| Mn(AHADMP)$_2$ | 0.26s | 0.18s |
| MnEDTMP | 0.23s | 0.13s |
| MnBDTMP | 0.19s | 0.13s |
| MnMDTMP | 0.08s | 0.06s |
| MnMXDTMP | 0.13s | 0.11s |
| GdMXDTMP | 0.06s | 0.06s |

The $^{31}$P study shows few differences between ligand all except (AEDMP) binding about 80% to hydroxy apatite and the figures are not significant when one realises the large errors in quantitation in NMR.

The binding of metal complexes do show differences and this experiment is such that these figures are significant. Small changes in ligand structure give different binding and the model separates the complexes on adsorption characteristics.

The last set of results shows that the complexes once bound still give relaxation of water molecules. The reduction is very significant and indicates the utility of these compounds in vivo. The differences in $T_1/T_2$ for different complexes may be useful to decide which complexes would give rise to good $T_1$ relaxation changes with the least loss of signal intensity.

This hydroxy apatite experiment indicates that the complexes will bind to calcified tissue in vivo, and will act in bound form as effective contrast agents for investigating calcified tissue by NMR screening. But the hydroxy apatite-complex adducts are likely to have utility of their own. After oral administration, they are likely to permit NMR imaging of the gastrointestinal tract. For this purpose the adducts compare favourably with those described in EPA 183760.

What is claimed is:

1. A method of investigating calcified tissue, which method comprises administering to a human patient a complex formed between (a) an amino di- or poly-phosphonate in which phosphonate groups comprise different carbon atoms, and (b) a paramagnetic metal ion, and thereafter subjecting the patient to NMR scanning.

2. A method as claimed in claim 1, wherein the di- or poly-phosphonate contain the groups —N(CH$_2$PO$_3$H$_2$)$_2$.

3. A method as claimed in claim 1, wherein the poly-phosphonate has the general formula NX$_2$CH$_2$PO$_3$H$_2$, where the two groups X are the same or different and each is —CH$_2$PO$_3$H$_2$ or —(CH$_2$)$_n$ N(CH$_2$PO$_3$H$_2$)$_2$, and n is up to 10, or a non-toxic salt thereof.

4. A method as claimed in claim 3, wherein the poly-phosphonate is ethylenediamine tetramethylphosphonate.

5. A method as claimed in claim 1, wherein the poly-phosphonate is meta-xylene-diamine tetramethylphosphonate.

6. A method as claimed in claim 1, wherein the paramagnetic metal ion is Gd(III).

7. A method as claimed in claim 6, wherein the complex is formed from (a) ethylenediamine tetramethylphosphonate and (b) Gd(III) in a molar ratio of (a) to (b) of at least 1.5.

8. A method as claimed in claim 7, wherein the complex is present in solution at a concentration of from 1 to 20 mM with respect to Gd.

9. A method as claimed in claim 1, wherein there is injected into the patient from 1 to 100 ml of an aqueous solution of the complex that is from 0.1 mM to 250 mM with respect to the paramagnetic metal ion.

10. An adduct comprising hydroxy apatite and a complex formed between (a) an amino di- or poly-phosphonate in which phosphonate groups are comprised of different carbon atoms, and (b) a paramagnetic metal ion.

11. An adduct comprising hydroxy apatite and a complex formed between (a) a di- or poly-phosphonate having the formula

or

where each of Y and Z is an aliphatic or aromatic group containing 1 to 12 carbon atoms including at least one continuous chain of 3 or more carbon atoms, which group may also contain one or more hydroxyl, ether, carboxylate, sulphonate, amine or aminomethylphosphonate groups, or a non-toxic salt thereof, and (b) a paramagnetic metal ion.

12. The adduct as claimed in claim 11, wherein the paramagnetic metal is $GD^{3+}$.

13. A complex formed from meta-xylene-diamine tetramethylphosphonic acid or a non-toxic salt thereof, and $Gd^{3+}$.

14. A method for investigating calcified tissue by NMR scanning, which comprises employing as a contrast agent, a complex formed between (a) an amino di- or poly-phosphonate in which phosphonate groups are comprised of different carbon atoms, and (b) a paramagnetic metal ion.

15. The method as claimed in claim 14, wherein the di- or poly-phosphonate contains the group —N(CH$_2$PO$_3$H$_2$)$_2$.

16. The method as claimed in claim 14, wherein the poly-phosphonate has the general formula NX$_2$CH$_2$PO$_3$H$_2$, where the two groups X are the same or different and each is —CH$_2$PO$_3$H$_2$ or —(CH$_2$)$_n$N(CH$_2$PO$_3$H$_2$)$_2$, and n is up to 10, or a non-toxic salt thereof.

17. The method as claimed in claim 16, wherein the poly-phosphonate is ethylenediamine tetramethylphosphonate.

18. The method as claimed in claim 14, wherein the poly-phosphonate is meta-xylene-diamine tetramethylphosphonate.

19. The method as claimed in claim 14, wherein the paramagnetic metal ion is Gd(III) or Fe(III).

20. The method as claimed in claim 19, wherein the complex is formed from (a) ethylenediamine tetramethylphosphonate and (b) Gd(III) in a molar ratio of (a) to (b) of at least 1.5.

21. The method as claimed in claim 20, wherein the complex is present in solution at a concentration of from 1 to 20 mM with respect to Gd.

* * * * *